United States Patent [19]

Domb et al.

[11] Patent Number: 5,344,411
[45] Date of Patent: Sep. 6, 1994

[54] METHOD AND DEVICE FOR INHIBITING HIV, HEPATITIS B AND OTHER VIRUSES AND GERMS WHEN USING A CATHETER IN A MEDICAL ENVIRONMENT

[75] Inventors: Abraham J. Domb, Efrat, Israel; Alain H. Shikani, Ruxton, Md.

[73] Assignee: Leonard Bloom, Towson, Md.; a part interest

[21] Appl. No.: 147,049

[22] Filed: Nov. 3, 1993

Related U.S. Application Data

[63] Continuation-in-part of Ser. No. 998,773, Dec. 22, 1992, which is a continuation of Ser. No. 661,699, Feb. 27, 1991, abandoned.

[51] Int. Cl.$^5$ ............................................. A61M 5/32
[52] U.S. Cl. ...................................... 604/265; 604/891.1; 128/207.14; 623/11
[58] Field of Search ................... 128/207.14, 207.15; 604/890.1, 891.1, 892.1, 96, 264, 265, 280; 623/1, 11, 12

[56] References Cited

U.S. PATENT DOCUMENTS

| | | | |
|---|---|---|---|
| 3,235,446 | 2/1966 | Shelanski et al. | 167/17 |
| 3,401,005 | 9/1968 | Katz | 8/115.5 |
| 3,566,874 | 3/1971 | Shepherd et al. | 128/349 |
| 3,598,127 | 8/1971 | Wepsic | 128/349 |
| 4,054,139 | 10/1977 | Crossley | 128/260 |
| 4,094,967 | 6/1978 | Gilbert | 424/28 |
| 4,113,851 | 9/1978 | Leveen et al. | 424/28 |
| 4,186,745 | 2/1980 | Lewis et al. | 128/349 R |
| 4,381,380 | 4/1983 | Leveen et al. | 604/265 |
| 4,603,152 | 7/1986 | Laurin et al. | 604/265 |
| 4,642,104 | 2/1987 | Sakamoto et al. | 604/264 |
| 4,650,488 | 3/1987 | Bays et al. | 623/12 |
| 4,879,135 | 11/1989 | Greco et al. | 427/2 |
| 4,917,686 | 4/1990 | Bayston et al. | 604/265 |
| 4,950,256 | 8/1990 | Luther et al. | 604/265 |
| 4,994,047 | 2/1991 | Walker | 604/264 |
| 5,013,306 | 5/1991 | Solomon et al. | 604/265 |
| 5,019,096 | 5/1991 | Fox, Jr. et al. | 604/265 |
| 5,019,601 | 5/1991 | Allen | 604/265 |
| 5,028,597 | 7/1991 | Kodama et al. | 514/56 |
| 5,061,254 | 10/1991 | Karakelle et al. | 604/265 |
| 5,071,648 | 12/1991 | Rosenblatt | 424/78.06 |
| 5,102,401 | 4/1992 | Lambert et al. | 604/264 |
| 5,156,164 | 10/1992 | LeVeen et al. | 128/832 |
| 5,165,952 | 11/1992 | Solomon et al. | 604/265 |

*Primary Examiner*—C. Fred Rosenbaum
*Assistant Examiner*—Chalin Smith
*Attorney, Agent, or Firm*—Leonard Bloom

[57] ABSTRACT

An anti-infective coating for a catheter or other medical device. The coating is insoluble in a biological medium and is bound to the surfaces of the catheter. The coating is a biocompatible, non-hydrogel polymer. One embodiment is a coating on the catheter which is complexed with an iodine solution to provide a programmed rapid release of iodine. A second embodiment is a solution of the biocompatible hydrogel polymer in which the iodine is dissolved and the solution containing iodine is coated in the catheter to provide a matrix having programmed sustained release of iodine. A coating with complexed iodine may be deposited over a coating with matrixed iodine to provide an anti-infective coating on a catheter with a rapid release and a sustained release of iodine over a period of weeks. A non-iodized polymer coating may be deposited on the complexed coating, the matrixed coating or the combined coating to provide protection to the sub coating and to further control the rate of release of iodine. The iodine containing coating provides a concentration of iodine that has sufficient activity and is available for a period of time which is long enough to allow the human immunodeficiency virus, bacteria, fungi and other germs to be inactivated. The coated device is stable and has long shelf life.

7 Claims, 8 Drawing Sheets

METHOD AND DEVICE FOR INHIBITING HIV, HEPATITIS B AND OTHER VIRUSES AND GERMS WHEN USING A CATHETER IN A MEDICAL ENVIRONMENT

CROSS-REFERENCE TO RELATED APPLICATIONS

The present application is a continuation-in-part of U.S. patent application, Ser. No. 07/998,773 filed Dec. 22, 1992 which is a file wrapper continuation of Ser. No. 07/661,699 filed Feb. 27, 1991 now abandoned, the contents of which are hereby incorporated herein in their entirety. The present application is related to application Ser. No. 08/092,114 filed Jul. 14, 1993.

FIELD OF THE INVENTION

The present invention relates to catheters and other medical devices. In particular, the present invention relates to catheters and implantable devices that are coatable with an iodine released anti-infective, programmable polymeric dispersion and solution for inhibiting infection induced by the catheters which are disposed and positioned in a human body.

BACKGROUND OF THE INVENTION

Catheters are commonly utilized especially by physicians and other health care personnel for various purposes, such as the long and short term intravenous delivery (infusion) and withdrawal of fluids, such as nutrients, blood and blood products for treatment and monitoring of the patient. Examples of catheters include venous catheters, Swan-Ganz catheters, double and triple lumen central catheters, arterial catheters, arterial line monitoring catheters and foley bladder catheters, to name but a few.

Regardless of the type of catheter, each has in common the fact that, during use, they are at least partly inserted or otherwise disposed and maintained within a patient's body. For example, venous catheters are directly inserted into the vein of a patient. This is achieved by first properly aligning of the catheter with the target vein. Once properly aligned, the venous catheter is pushed (directly inserted) through the patient's skin, and into their vein. Other catheters such as closed suction drainage catheters and penrose drains are inserted into body wounds. Other catheters are inserted into body cavities such as the urinary tract (the foley bladder catheter), the aero-digestive tract (endotracheal tubes and tracheotomy tubes), nasal-gastric tubes, etc.

Two problems may arise when these catheters and medical devices are exposed to blood and/or body fluids. Droplets of the blood and/or body fluid remain on the catheter after its use and removal from the patient. If the patient is a carrier of a potentially infectious germs such as the human immunodeficiency virus (HIV) and the hepatitis B virus (HBV), the infection may be transmitted to other individuals who subsequently contact the contaminated catheter or medical device. If these individuals happen to have an abrasion in their own skin, they may become infected with these germs.

Two pathogenic germs that have been shown to be present in a potentially infective state in the blood and almost all the body fluids of infected patients are HIV and HBV. Because of the logarithmic increase in the number of people that carry either of these two viruses, a serious public health problem has arisen. Although the HIV is not capable of withstanding exposure to wide ranges of temperature and humidity changes, it is stable enough in the droplets of blood to remain viable and retain infectivity for more than three days if dried and held at room temperature, and for more than a week in an aqueous environment at room temperature. HBV is even more resistant and remains viable at room temperature for 6 months. Other germs that carry similar potential infectivity include hepatitis C, D and E, different bacteria, mycobacteria and fungi.

The enormous amount of medical waste generated by hospitals, clinics and laboratories must be disposed of in specially designed containers in order to avoid transmission of germs to health care providers. All health care professionals are required to observe the "Universal Blood and Body Fluid Precautions" developed by the Center for Disease Control in 1985. A study made by the Center for Disease Control established that the chances of health care workers acquiring HIV through accidental transmission from infected individuals is roughly one out of three hundred.

Another significant problem is that contaminated catheters and medical devices represent a potential hazard to the general public as well as to health care providers and to workers engaged in disposal of medically contaminated waste. The presence of HIV and other infectious germs on catheters and medical waste is a potential source of infection to anyone contacting these materials. Procedures for proper disposal have been instituted but the problem has not been eliminated. A need exists for a means to inhibit the infective gems on catheters and contaminated waste to protect the health of all persons who may contact these products subsequent to contamination by diseased patients.

Infection and inflammation is perhaps most commonly encountered at the point where the catheter is inserted through the skin (which normally forms a natural barrier against such infectants), as well as along the catheter's length. Such infection and inflammation can result in swelling of both of the limb, such as the patient's arm, and of the vein itself. If the catheter is in body cavities, such as the bladder, ear or aero-digestive tract, infection and inflammation of these cavities may occur with formation of granulation tissue and blockage of these cavities. However, and more seriously, bacteria/fungi can also migrate into the patient's bloodstream or body organs resulting in bacteremia/fungemia or infection of the bloodstream, thereby spreading the infection throughout the patient's body. Such a condition can often be fatal, especially if the infection spreads to the patient's heart or other organs.

Further, if the catheter is positioned within the patient's body for a prolonged period of time, tissue growth (for example, granulation or fibrosis) may develop about the catheter, as a natural consequence of the body's natural defense mechanisms against the presence of the contaminant. Such tissue growth can be harmful to the patient by, for example, "adhering" the catheter to the vein. This condition can complicate removal of the catheter by causing the vein to be torn and ruptured when the catheter is removed, resulting in internal bleeding.

To compound the above-mentioned problems of infection, inflammation and tissue growth, often the only method of treating such problems is by the systemic administration of antibiotics, etc. Unfortunately, such systemic treatments can be costly, and can result in change of bacterial flora and emergence of resistance. Such systemic treatments can also decrease healing and have other undesirable side effects.

All-in-all, as can be readily understood, the above-mentioned problems of infection and inflammation represent grave problems of longstanding duration. These problems have curtailed the use of catheters, so that standard catheters can be utilized only for several days at a time before they must be removed and a new one inserted. Such a situation creates a further problem in that the insertion and removal of catheters (especially where central venous catheters are involved) can be a dangerous task.

Thus, the use of catheters presents potential problems to the environment of health care providers who must handle catheters which have been exposed to blood and other body fluids of patients, and also to the patient in whom the catheter is implanted who may become infected from germs on the catheter or introduced into the cavity in which the catheter is implanted.

It has been proposed to fight bacterial infection by incorporating and/or binding antibiotics and antimicrobial agents into various medical devices (such as catheters, bandages, implants, ocular inserts and interuterine devices) which are inserted into a patient's body. Once inserted, these antibiotic/antimicrobial agents are released or leeched therefrom for preventing infection. Examples of such devices are the catheters disclosed in U.S. Pat. Nos. 3,598,127 issued to Wepsic (a urinary tract catheter of nonpermeable rubber in which antibiotics, such as neomycin is infused); 4,186,745 (wherein antibacterial substances are infused into microporous polyethylene, polypropylene or polyfluorocarbon polymers); 4,054,139 issued to Crossley (wherein oligodynamic agents, such as metallic silver and other heavy metals are incorporated onto catheter surfaces); and 3,566,874 issued to Shepard (wherein antibiotics and germicides, such as penicillin and cetylpyridinium chloride are infused into a hydrophilic polymer for coating medical appliances). Other examples are disclosed in U.S. Pat. Nos. 4,603,152 issued to Lavrin; 4,642,104 issued to Sakamoto et al; 4,650,488 issued to Bays et al; 4,879,135 issued to Greco et al; 4,950,256 issued to Luthoer et al; 5,013,306 issued to Solomon et al; 5,028,597 issued to Kodama et al; 5,019,096 issued to Fox, Jr. et al; and 5,019,601 issued to Allen.

While being generally useful, in varying degrees, for their intended purposes of fighting infection on a localized level, each of these approaches suffers from one or more of the following disadvantages: (1) they merely involve mixtures and the antibacterial agent is neither chemically combined to the plastic nor slowly released; (2) the antibiotic/antimicrobial substances proposed are effective only against specific bacteria and not against aggressive microbes such as viruses (e.g., HIV and hepatitis); and (3) those disclosures involving bioerodible coatings present the undesirable side effect of also releasing the bioerodible coating into the patient's body with all of the attendant problems that that presents.

The use of a multi-layer cannula which is swellable and controls the rate of water passage through the layers and controls the diffusion of medicaments is disclosed in U.S. Pat. No. 4,994,047 issued to Walker et al.

Commonly-utilized and well-accepted for inhibiting infection is the use of iodine. Iodine is a broad spectrum antimicrobial agent that has bactericidal, fungicidal and viricidal properties. When iodine reacts with aqueous solutions, free iodine, which provides the germicidal effect, is released. While generally inhibiting infective germs over the short term, the biocidal effectiveness of iodine is dependent on, inter alia, how long the contaminant is exposed to it. This is particularly important in the case of HIV and HBV where the iodine is effective only after it remains in contact with the virus for a relatively long period of time (more than 10 minutes). Thus, over the long term, since topically applied iodine is released all at once, it does not provide adequate sustained protection. Further, such topical application is of little to no use in inhibiting internal infection either in the short term or in the long term.

To increase the effectiveness of iodine, it is normally incorporated into solutions, soaps, creams, pastes, etc., to form an iodophor. Such iodophors, in effect, provide a reservoir of iodine from which small amounts of free iodine in aqueous solution are released over a period of time. These iodophors are then topically applied to that area of a patient's body which is desired to be treated. Perhaps the best known of these iodophors is povidone-iodine, a compound of polyvinylpyrrolidone with iodine. An example of such an application can be found by reference to U.S. Pat. No. 4,010,259 issued to Johansson.

It has been disclosed to incorporate iodophors onto various medical paraphernalia for topical application. In U.S. Pat. Nos. 3,235,446 issued to Shelanski et al, iodinated polyurethane foams and films are incorporated into bandages and sponges. Similarly, U.S. Pat. No. 3,401,005 issued to Katz discloses fibrous materials (such as gauze) that are treated with combinations of polymers, halogens and iodine for use in bandages and surgical dressings. U.S. Pat. No. 4,094,967 issued to Gilbert discloses compositions method of binding iodine to polyvinylpyrrolidone with the use of cinnamic alcohol or tannic acid which is to be applied to matting, gauzes and foam rubber for topical use. U.S. Pat. No. 4,113,851 issued to Le Veen et al, discloses a composition of iodine, pyrrolidone polymer and a polymeric basic acid for incorporation into salve-ointments, dressings or bandages. U.S. Pat. No. 5,156,164 issued to Le Veen et al discloses a contraceptive sponge consisting of a polyurethane open cell foam impregnated with surfactant and iodine.

While being useful for their various purposes of generally inhibiting bacterial infection at the point of the insertion over the short term, all of those references disclose compositions into which the iodine has been complexed for topical application only.

U.S. Pat. No. 5,071,648 issued to Rosenblatt discloses films and sponges formed from polyvinyl alcohol complexed with iodine, which provides a controlled release of iodine.

It has also been disclosed in U.S. Pat. No. 4,381,380 issued to Le Veen et al, to provide cross-linked thermoplastic polyurethane articles, such as catheters, into which iodine has been complexed for antibacterial use. While being useful for their purpose, such cross-linked thermoplastics cannot be utilized for coatings.

As is well-known, polymers, such as polyurethanes, may be either essentially cross-linked or essentially uncross-linked. The uncross-linked polymers are suitable for the production of coatings, but are not of a tensile strength which is acceptable to fashion appliances, such as catheters, which require more exacting physical properties. The cross-linked polymers are suitable for the production of appliances, but are not suitable for the production of coatings, such as the ones noted herein. Further, cross-linked polymers possess a steric hinderance that renders inaccessible many, and sometimes all, of the linkages which complex with the iodine.

It would be extremely advantageous to provide a catheter which has a thermoset uncross-linked polymer coating that has iodine either complexed therein for quick and relative immediate release of the iodine and/or matrixed therein for sustained release of the iodine.

Thus, it can be seen that there remains a need for catheters that are solvent coatable with a polymeric dispersion or solution that have iodine complexed and/or matrixed therein, so as to provide for immediate and/or sustained release of the iodine therefrom for inhibiting infection, that is commonly associated with the use of such catheters.

SUMMARY OF THE INVENTION

It is the primary object of the present invention to provide a device and method whereby a catheter and other medical device, which have thereon a surface compatible polymer coating having iodine complexed and/or matrixed therein, so as to provide for the immediate and/or sustained release of the iodine therefrom for inhibiting dissemination of germs during use thereof.

It is a still further primary object of the present invention to provide a polymer coated catheter in which the iodine release is localized and programmable, as desired.

In accordance with the teachings of the present invention, there is disclosed an anti-infective coating for a catheter having a surface. The catheter is disposed and maintained within a body of a patient having blood or other body fluids. The anti-infective coating is insoluble in a biological medium and is bound to the surface of the catheter, during storage, use and initial disposal thereof. The anti-infective coating includes a biocompatible, non-hydrogel polymer. The polymer is compatible with and binds to a surface of the catheter. The polymer is soluble in an organic solvent. Iodine is complexed with the coating for programmed rapid release of the iodine from the coating when the catheter is disposed and maintained in the body of the patient and contacts blood or other body fluids.

A method is disclosed for preparing a programmed rapid release anti-infective coating for a catheter having a surface and being disposed and maintained within a body of a patient. The coating releases iodine for a period of time at a concentration sufficient to inhibit human immunodeficiency virus, hepatitis B virus and other germs. The anti-infective coating is insoluble in a biological medium and is bound to the surface of the catheter. A biocompatible, non-hydrogel polymer is dissolved in an organic solvent and the solution containing the polymer is applied to the surface of the catheter. The solvent is evaporated to form a uniform polymer coating on the catheter. The coated catheter is immersed into a solution of iodine and potassium iodide in water for approximately 0.03 to 60 minutes. The iodine complexed polymer coated catheter is dried.

There is also disclosed an anti-infective coating for a catheter in which iodine is matrixed with the coating for programmed sustained release of the iodine from the coating when the catheter is disposed and maintained within a body of the patient.

A method is disclosed for preparing a programmed sustained release anti-infective coating for catheter having a surface. The catheter is disposed and maintained within a body of a patient having blood and other body fluids. The coating releases iodine for a period of time at a concentration sufficient to inhibit human immunodeficiency virus, hepatitis B virus and other germs. The anti-infective coating is insoluble in a biological medium and is bound to the catheter. The catheter is cleaned. A solution of a biocompatible, non-hydrogel polymer is prepared in an organic solvent. Iodine is dispersed in the solution of the polymer. The polymer/iodine solution is applied to a surface of the catheter. The solvent is evaporated to form a uniform polymer/iodine coating on the catheter.

In still further accordance with the teachings of the present invention, there is disclosed in combination with a catheter intended to be disposed and maintained within a patient's body having body fluids, a substantially biocompatible, anti-microbial, anti-viral coating on the surface of the catheter. The coating is fully compatible with the normal use of the catheter and includes a non-hydrogel polymer having dispersed therein a solid solution of iodine. The iodine has a programmable timed release when exposed to body fluids, and the coating remains substantially on the catheter during storage, use and initial disposal thereof.

A method is disclosed for preparing a programmed release anti-infective multiple coating for a catheter having a surface. The catheter is disposed and maintained within a body of a patient having blood and other body fluids. The coating releases iodine for a period of time at a concentration sufficient to inhibit human immunodeficiency virus, hepatitis B virus and other germs. The anti-infective coating is insoluble in a biological medium and is bound to the surface of the catheter. The catheter is cleaned. A solution of a first biocompatible, non-hydrogel polymer in a first organic solvent is prepared. Iodine is dispensed in the solution of the polymer. The polymer/iodine solution is applied to the surface of the catheter. The first organic solvent is evaporated to form a uniform first polymer/iodine coating on the surface of the catheter. A second biocompatible, non-hydrogel polymer is dissolved in a second organic solvent to form a second solution. The second solution containing the polymer is applied to the first polymer/iodine coating on the catheter. The second solvent is evaporated to form a second uniform polymer coating on the catheter. The coated catheter is immersed into a solution of iodine and potassium iodide in water for approximately 0.03 to 60 minutes. The iodine complexed polymer coated catheter is dried. The outer coating provides short term programmable timed release of iodine and the inner coating provides long term programmable release of iodine.

There is further disclosed a method of inhibiting HIV, hepatitis B virus, and other viruses and germs when using an instrument during a medical procedure on a patient. A catheter and/or medical device is provided and coated with an anti-infective coating of a polymer having iodine therein. The coated catheter is inserted within the patient's body such that the coating in the catheter contacts a fluid in the patient's body to release iodine from the coating. The catheter is removed from the patient's body and the catheter is disposed.

These and further objects and advantages of the present invention will become readily apparent from a reading of the following description and examples, taken in conjunction with the enclosed drawings.

DESCRIPTION OF THE PREFERRED EMBODIMENTS

Figure 1:
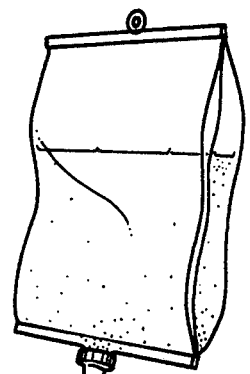
FIG. 1 illustrates the use of a catheter in its environment to infuse fluids into the vein of a patient.

Referring now to FIG. 1, an implantable catheter 10 such as a venous catheter, a bladder-foley catheter, an endotracheal tube, a tracheotomy tube, a nasal gastric tube, a closed suction drainage device, a penrose drain, a nasal stent, an ear ventilation tube and similar devices are inserted directly through the skin of a patient or into a body orifice. The catheter 10 also may be connected to a container holding fluid to be infused into the patient.

Figure 2:
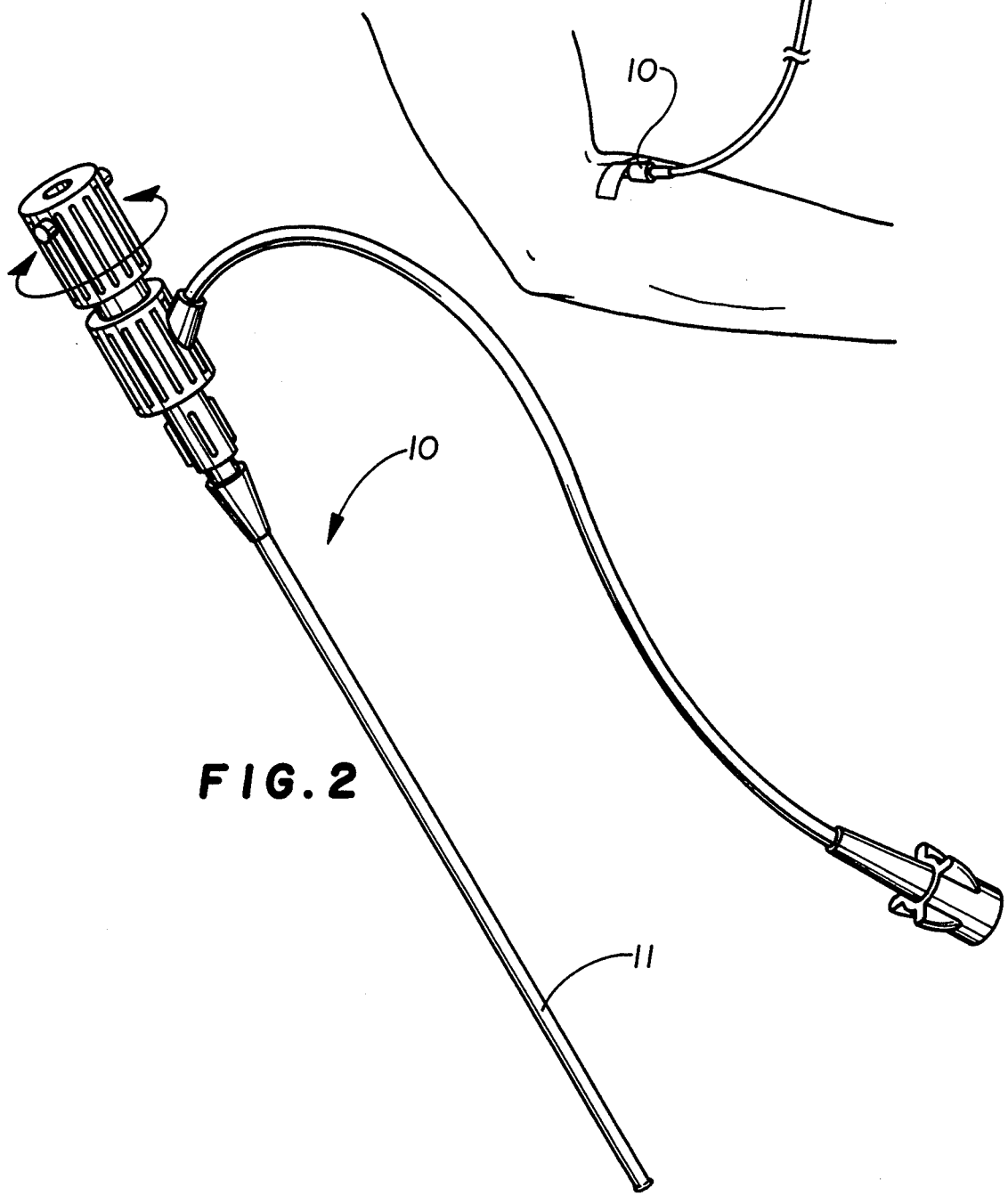
FIG. 2 is a perspective view of a typical catheter showing the coating on the surface.

The catheters 10 of the present invention, are standard catheters which have biocompatible, non-hydrogel polymer coating(s) 11, 12 and 13 thereon. Commonly, these catheters 10 are fabricated from a plastic material (FIG. 2).

The coated catheter 10 of the present invention is useful with humans and with any living creature in which a catheter may be inserted and in which control of viruses and germs is desired.

In order to avoid the problems of infection discussed above, the polymer coating(s) 11 and 12 have elemental iodine matrixed and/or complexed therein. Water in the fluids that are naturally present in the patient's body contact the iodine, dissolving the iodine from the coating(s) 11 and 12. In this manner, a programmable sustained and/or (controlled) immediate release of the iodine from the coating(s) 11 and 12 respectively, is provided.

It is noted that the polymer-iodine coatings 11 and 12 on the catheter 10 of the present invention provide localized delivery of iodine at relatively high concentrations in the immediate area which is critically affected. The released iodine is then available to kill and/or otherwise inhibit the microbe, including bacteria and viruses, that can result in infection. Finally, the release of the iodine from the coatings 11 and 12 is programmable, so that it may occur either immediately or in a controlled, sustained manner over a prolonged period of time ranging from a few minutes to several weeks or longer.

Pursuant to the teachings of the present invention, the polymers used in the coatings 11, 12 and 13 of the present invention exhibit the following traits: (1) the polymers are soluble or dispersible in solution in order to be disposed onto the surface of the catheter 10 (in this regard, it is noted that thermoplastic and cross-linked polymers that are insoluble are not useful); (2) the polymers do not chemically react with iodine; (3) the polymers are compatible with iodine, so as to form a uniform, solid complex or matrix with the iodine; (4) the polymers are capable of adhering to the surface of the catheter 10; (5) the polymers are capable of forming a uniform coating on the surface of the catheter 10; and (6) the polymers are capable of forming polymer-iodine complexes and matrixes which remain stable during storage, so as to avoid a significant loss of iodine therefrom.

All of these polymers are biocompatible, so as to not cause or result in adverse reactions in the patient's body. Furthermore, all of these polymers are nonbioerodible, so that they are not inadvertently released into the patient's body. The polymers are insoluble in water and/or body fluids and remain bound to the catheter's surface even after the iodine in the respective coatings has been released. The polymers of the present invention are non-hydrogel insofar as the polymers swell only slightly when in contact with water. This is distinguished from polymers such as polyvinyl alcohol and polyurethane diacrylate which, after exposure to water, may swell up to 100% of the volume prior to exposure to water. This consideration is one factor which permits multiple coatings of the present invention as will be described. A polymer which swells cannot be used in the present invention as a base for another polymer to be coated over the base coating. The polymers preferably have a molecular weight of more than 1,000.

In this manner, the polymers of the present invention are distinguishable from previous coatings such as the polyvinyl alcohol coating of Rosenblatt (U.S. Pat. Nos. 4,381,380 and 5,156,164) which is water soluble and is removed from the surface of a device by dissolution when in contact with body fluids. Also, the referenced coatings are not soluble in organic solvents so a permanent coating cannot be formed from an organic solvent. The present invention also differs from the hydrophilic material of Walker (U.S. Pat. No. 4,994,047) which swells when contacted with an aqueous liquid.

The polymers utilized in the iodine complexed coating 11 is preferably polyurethane or polyurea. The polymers utilized in the iodine matrixed coating 12 is selected from the group consisting of polyurethane, ethylene vinyl acetate, polyvinylchloride, polyesters, nylon, polycarbonate, polyethylene, polymethyl methacrylate, cellulose esters (like ethyl, methyl and propyl), polypropylene, polystyrene, polytereflouroethylene, polyvinylchloride, poly(ethylenevinyl acetate), elastomeric organosilicon polymers, poly(hydroxy alkyl esters), copolymers and combinations thereof.

Preferably, the coatings 11, 12 and 13 are between 0.01 and 1.0 mm in thickness and, most preferably, between 0.1 and 0.22 mm in thickness.

The polymer coatings may be formed by solvent casting or melting. The polymer coatings 11, 12 and/or 13 are applied to the surfaces of the catheters by dipping, spraying, brush coating, or any other suitable methods.

The iodine utilized herein is elemental iodine. As shall be discussed at greater length below, the iodine may be incorporated into the polymer coatings 12 and 11 either by matrixing at the time of manufacture (casting or melting), or subsequently thereto, by complexing such as by absorption therein to obtain a solid solution of the iodine. The solid solution is a mixture or distribution of iodine molecules within the polymer chains. This solid solution is differentiated from a physical mixture of iodine particles dispersed in the polymer.

In the catheters 10 of the present invention, the polymer/iodine complexes 11 are formed by complexing the iodine with the polymer coating after the polymer coating has been applied to the surface of the catheter 10. This can be achieved by spraying, dipping or painting an iodine solution on the catheters 10 that already have the polymer coating thereon. Iodine release occurs by decomplexation or desorption of the iodine as a result of an equilibrium between the polymer coating 11 and the surrounding medium. Since iodine in a polymer-iodine complex may be easily contacted and dissolved by the water in the body's natural fluid, the release of complexed iodine from the iodine-polymeric coatings 11 of the present invention occurs relatively fast (within several minutes). Iodine can be complexed and loaded by immersing the polymer-coated catheters in an iodine solution in water or alcohol. The kind of polymers that are capable of complexing iodine are those that contain urethane or urea bonds.

In the catheters 10 of the present invention, the polymer/iodine matrixes are formed by dissolving solid elemental iodine into the polymer solution to form the polymer-iodine matrix. The polymer-iodine matrix is then subsequently formed onto a surface of the catheters 10 by spraying, dipping or painting the surface with the polymer-iodine matrix solution. The iodine is released from the polymer matrix by diffusion as a result of water penetrating into the matrix, dissolving the iodine and carrying it out into the surrounding medium. Since, it is more difficult (as compared to complexed iodine) for matrixed iodine to be contacted and dissolved by the water in the body's natural fluids, the release of matrixed iodine from the polymeric coating 12 is more sustained than is the release of complexed iodine from the polymeric coating 11.

Figure 3:
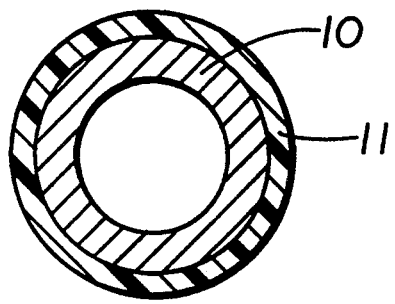
FIG. 3 is a cross-section view of a first embodiment of the present invention (not to scale) wherein iodine is complexed into a polymer coating on the catheter for the release of the iodine from the coating to inhibit infection.

With particular reference now to FIG. 3, the first preferred embodiment of the catheter 10 of the present invention is illustrated. In the first embodiment, a polymer coating 11 is directly disposed on the surface of the catheter. The polymeric coating 11 has iodine complexed therein. Complexing of the iodine in the polymeric coating 11 means that the iodine may be easily contacted and dissolved by the water in the body's natural fluid for quickly immediately releasing the iodine from the polymeric coating 11. FIG. 3 is not drawn to scale in order to more clearly show the coating 11.

Figure 4:
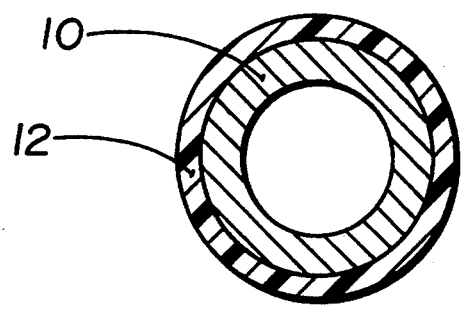
FIG. 4 is a cross-section view of a first embodiment of the present invention (not to scale) wherein iodine is matrixed into a polymer coating on the catheter for the release of the iodine from the coating to inhibit infection.

The second preferred embodiment of the catheters 10 of the present invention are illustrated in FIG. 4. In this second embodiment, a polymer coating 12 is directly disposed on the surface of the catheter 10. The polymeric coating 12 has iodine matrixed therein. As will be readily understood by those skilled in the art, matrixing (as opposed to complexing) of the iodine makes contact of the iodine with water in the body's natural fluids (contact that would dissolve the iodine) more difficult. In this manner, the release of the iodine from a polymer coating 12 in which it is matrixed, is slower than that of complexed iodine, so that the matrixed iodine release is sustained and controlled. FIG. 4 is not shown to scale in order to more clearly show the coating 12.

Figure 5:
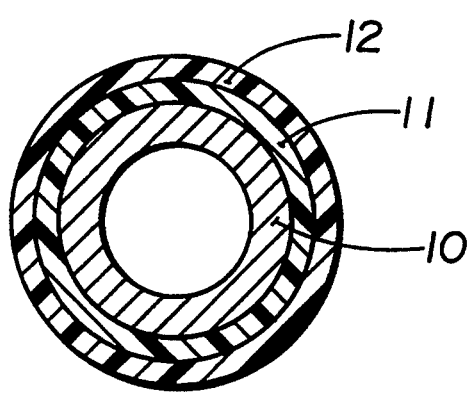
FIG. 5 is a cross-section view of an embodiment of the catheter of the present invention (not to scale) wherein iodine is matrixed into a biocompatible, non-hydrogel polymer inner coating on the catheter for the programmable (controlled) sustained release of iodine from the inner coating, and further wherein iodine is complexed into a biocompatible, non-hydrogel polymer outer coating on the catheter for the programmable immediate release of iodine from the outer coating to inhibit infection.

With particular reference now to FIG. 5, the third preferred embodiment of the catheters 10 of the present invention is illustrated. In the third embodiment, a first, inner polymer coating 12 is directly disposed on the surface of the catheter 10. The inner polymeric coating 12 has iodine matrixed therein. A second, outer coating 11 is disposed on the inner coating 12. The outer polymeric coating 11 has iodine complexed therein. In this fashion, such a two-layer polymeric coating provides both an immediate release (from the complexed coating) as well as a continuous and sustained release (from the matrixed coating) of iodine therefrom. FIG. 5 is not drawn to scale in order to more clearly show the coatings 11, 12.

In this regard, it is noted that the presence of the outer coating 11 acts to further shield the iodine in the polymer-iodine matrix of the inner coating 12 from the water in the body's natural fluids. In this fashion, the release of the matrixed iodine from the inner coating 12 may be programmed, so as to be further slowed. This feature provides an even greater sustained release of the iodine therefrom than is available from the single polymer-iodine matrix coating 12 of FIG. 4. In this manner, infection of the body about the coated catheter 10 of the present invention is inhibited over a longer period of time.

Figure 6:
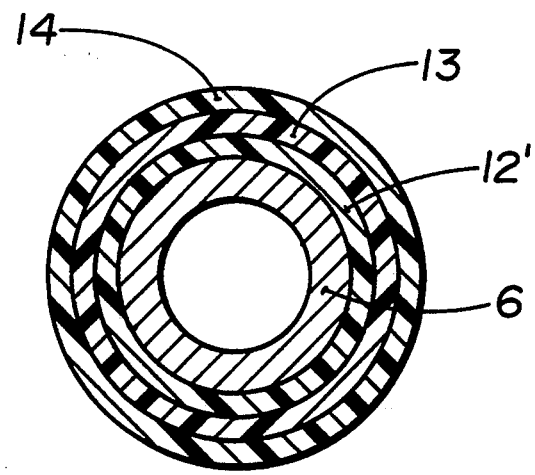
FIG. 6 is a cross-section view of another embodiment of the catheter (not to scale) wherein inner coating and outer coating of FIG. 5 further is coated with a polymer having no iodine therein.
Figure 7:
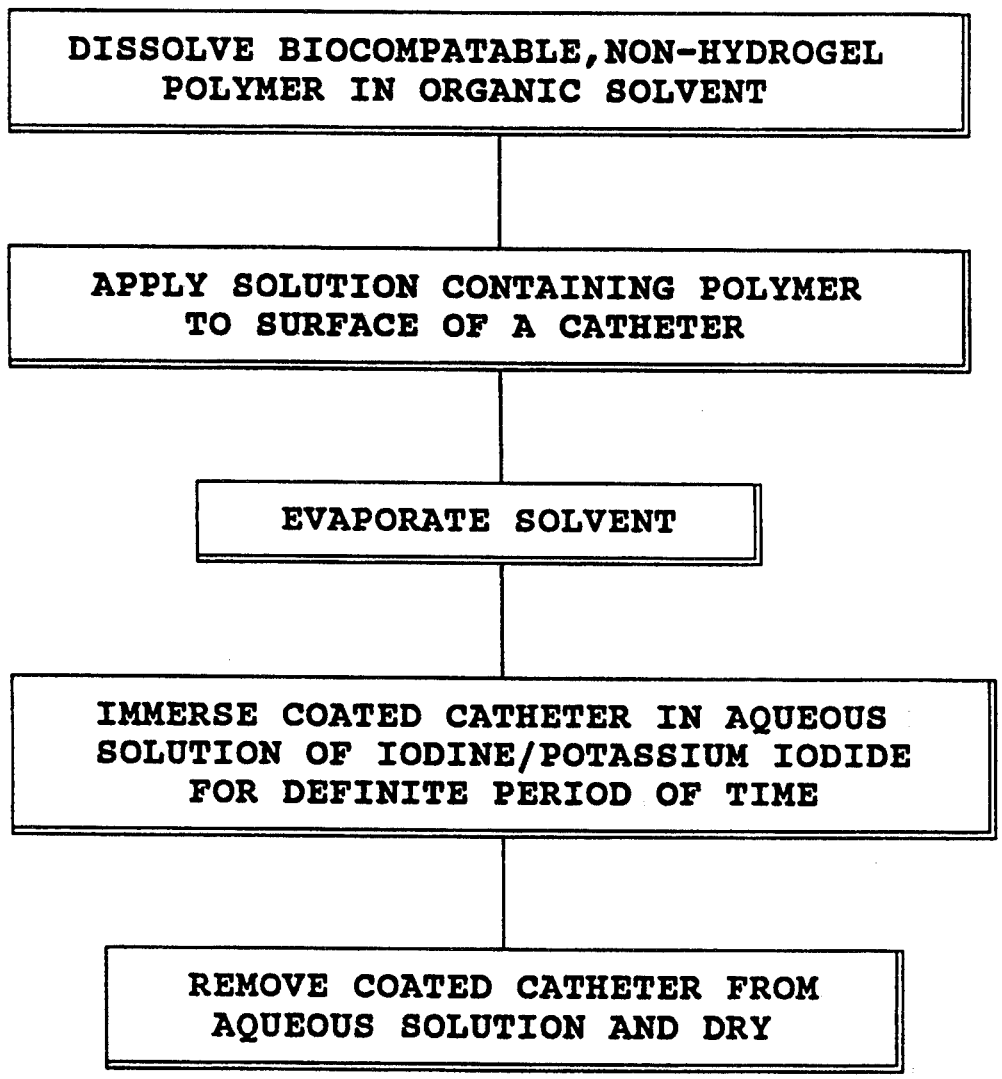
FIG. 7 is a block diagram showing the method of preparing the matrixed coating.
Figure 8:
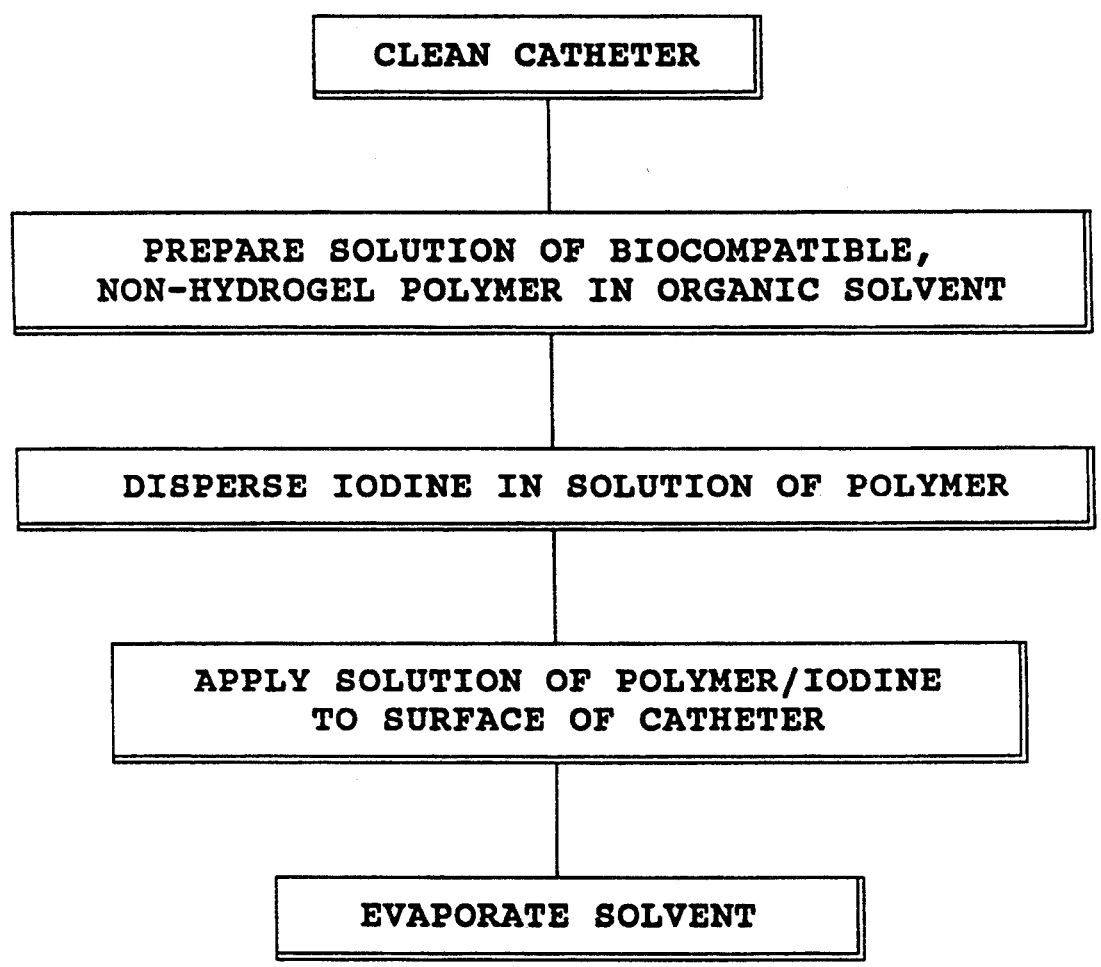
FIG. 8 is a block diagram showing the method of preparing the complexed coating.
Figure 9:
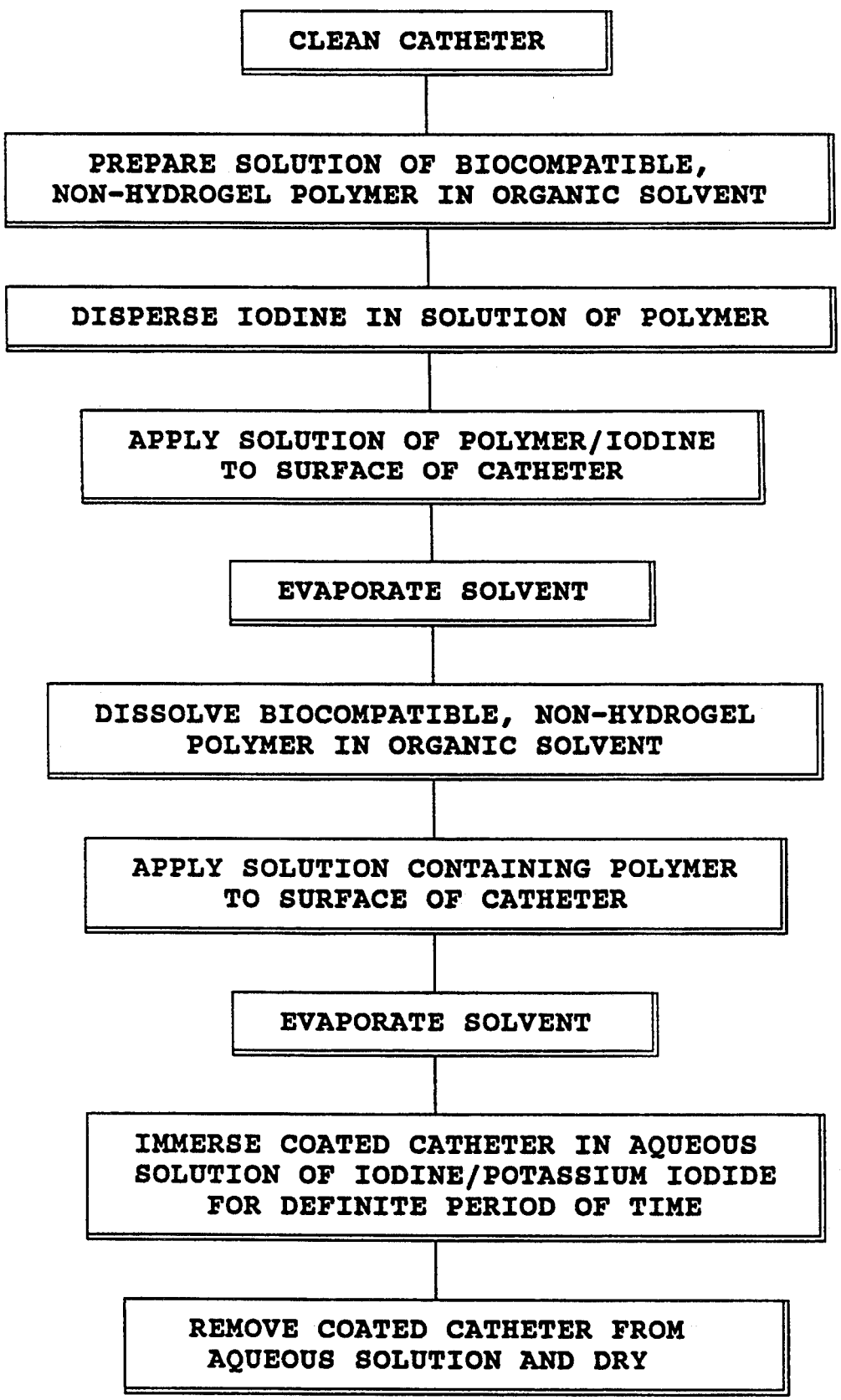
FIG. 9 is a block diagram showing the method of preparing the complexed coating over a matrixed coating.
Figure 10:
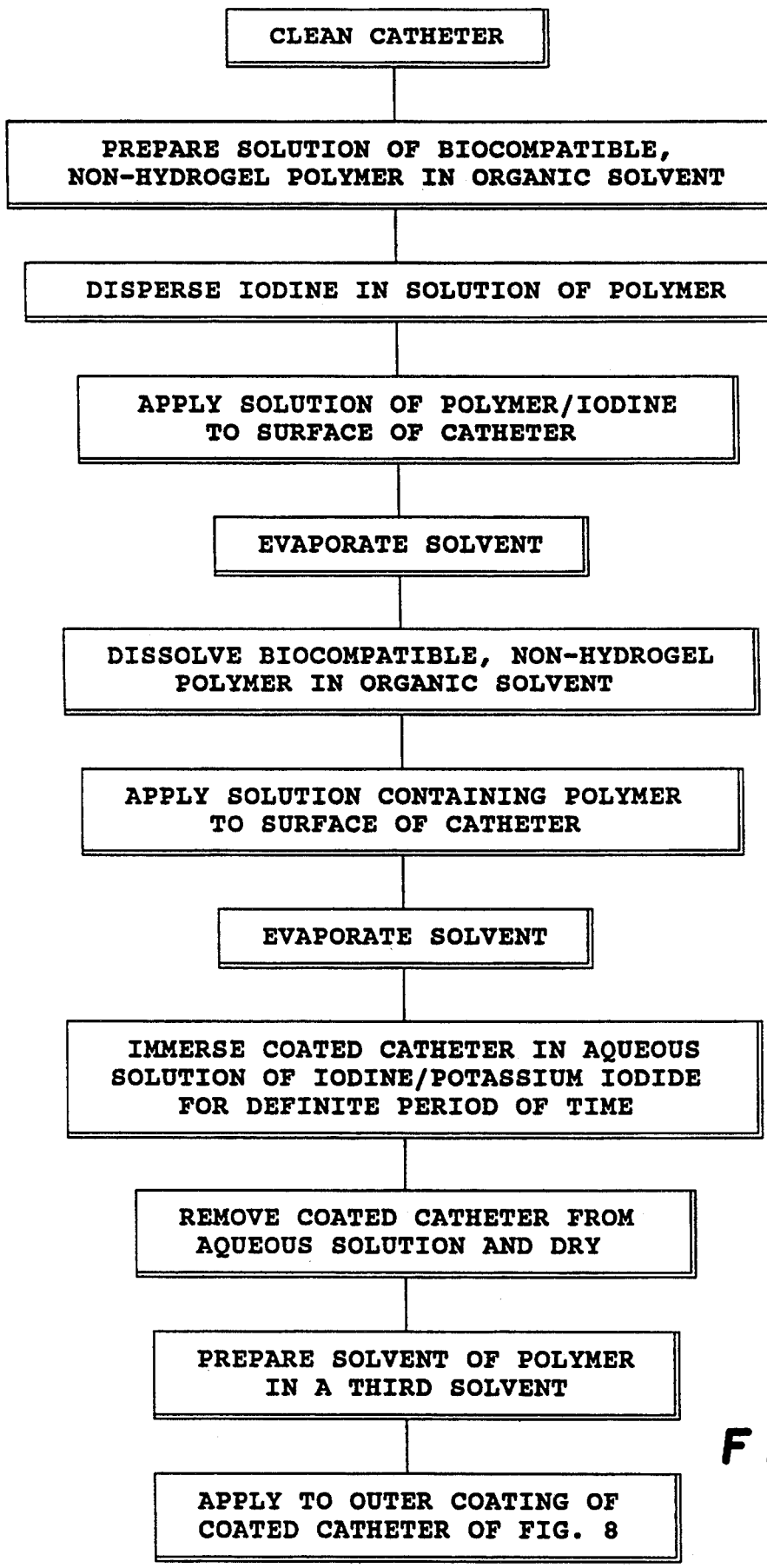
FIG. 10 is a block diagram showing the method of applying a coating without iodine to the coating of FIG. 9.

Referring to FIG. 6, if desired, any of the three aforementioned embodiments of the catheters 10 of the present invention may further include a non-iodized polymer coating 13 that is disposed, respectively, on either the complexed coating 11 or on the matrixed coating 12. Provision of this non-iodized polymer coating 10 acts to further shield the iodized coatings 11 and/or 12 from the water in the patient's natural bodily fluids (which contact and dissolve the iodine). In this fashion, the release of the iodine from the coatings 11 and/or 12 may be still further programmed in order to provide a more precise and sustained release of the iodine. The coating is stable at shelf conditions and will not start releasing iodine until it is in contact with body fluids or other fluids.

As has been mentioned above, in the catheters 10 of the present invention, programmability of iodine released from the coatings 11 and 12 is provided by controlling the release of the iodine from the polymeric complex or matrix. In this regard, it is noted that release is a function of, and varies according to, the thickness, concentration, chemical composition and solubility of the polymer from which the coating 11 or 12 is fabricated. Thus, variation of any or all of these factors may be resorted to in order to program the release of the iodine therefrom.

The variation of the polymer coating thickness alters the release of iodine from the polymer-iodine complexes/matrixes, in that the thicker the coatings, the slower and more sustained will be the release of the iodine from the iodine-polymer complexes and matrixes. This is achieved by the fact that thicker coatings make the contact between the iodine and the water in bodily fluids more difficult to achieve. Control of the thickness of the coating can be achieved by subsequent dippings, dipping the device in polymer having higher concentrations of iodine or by spraying/brushing a thicker coating of the polymer-iodine solution on the surface. The initial release rate is approximately constant irrespective of the thickness of the coating. The non-iodized coating 13 may also be viewed as a rate limiting coating. The thicker the rate limiting coating 13, the slower is the release rate of iodine and the delay time increases as the thickness of the rate limiting coating 13 increases.

The variation of the concentration (or loading) of iodine in the polymer-iodine complexes 12 and matrixes 13 alters the release of iodine from the polymer-iodine complexes/matrixes 11/12, respectively, in that the higher the loading of iodine, the more immediate and more sustained will be the release of the iodine from the polymer-iodine complexes 11 and matrixes 12. In this regard, iodine loading varies from 0.01% mg iodine/mg polymer (wt/wt) to 40% mg iodine/mg polymer (wt/wt). The preferred loading value is approximately 0.1% to 25%. To obtain these loading values, the iodine-polymer coating solution is more concentrated with respect to iodine to compensate for evaporation of iodine during the coating process.

The composition of the polymer-iodine coatings 11 and 12 may alter the release of iodine from the polymer-iodine matrixes/complexes 13 and 12, respectively, by altering the release profile of the iodine therefrom or to increase the shelf life stability of the iodine in the coating. In this respect, the coatings 11, 12 and 13 may further contain various additives, such as inorganic or organic salts, complexing molecules, such as pyrrolidone derivatives, and natural and synthetic oils. For example, to increase the iodine release rate, a fine powder of potassium iodide (KI) or sodium chloride (NaCl) is added to the polymer-iodine coating solution prior to coating of the catheter 10 by dipping or spraying. To retain the iodine in the coating and slow the iodine release rate, oligomers and polymers such as vinylpyrrolidone, urea and cellulose may be incorporated in the polymer-iodine complexes and matrixes. In this respect, incorporation of such additives aids in making the release of the iodine from the polymer-iodines complexes/matrixes programmable. A hydrophilic additive, such as polyethylene glycol, increases the release rate since it increases the water penetration into the polymer coating and subsequently increases the leach out of the iodine. In particular, addition of 10% of a polyethylene glycol (PEG 600) decreases the t ½ of an ethyl vinyl acetate coating from 36 hours to 26 hours. If, for example, polyvinylpyrrolidone-iodine complex is used, the release rate will decrease because iodine is complexed and is not free to be released by simple diffusion. In addition to elementary iodine, the polymer may contain anti-inflammatory agents such as steroids and non-steroidal anti-inflammatory agents, such as ibuprofen, naproxen and indomethacin, or antibiotics, such as aminoglycosides, penicillins, cephalosporins, polymyxin, ofloxacillins or anti-fungals such as mycostatic, griseofulvin and ketoconazole. It also may contain anti-thrombogenic drugs such as heparin, prostaglandins and warfarin.

The catheters 10 of the present invention will be further understood by reference to the following examples and FIGS. 7-10 which are meant to be illustrative, but not limitative, thereof:

EXAMPLE 1

Polyurethane Coating With Iodine Matrixed Therein

An iodine matrixed polyurethane coating is prepared by dissolving 0.5 grams of iodine crystals in a tetrahydrofuran solution containing 1.5 grams of segmented polyurethane (Estane, TM, Goodrich, Cleveland, Ohio).

Coating is achieved by dipping the catheter in the polyurethane-iodine matrix solution. After solvent evaporation, the resulting dark uniform coating of about 0.2 mm may be further coated with a noniodized Ethylene Vinyl Acetate (EVAc) coating by further dipping the polymer-iodine matrix coated needle or cutting blade in a chloroform solution of EVAc. The resultant EVAc coating of 0.05 mm aids in preventing iodine release from the polymer-iodine matrix coating by sublimation. Alternately a solution of polyurethane in acetone (2 weight %) containing iodine (0.05%) was sprayed over various surfaces using a Sigma Spray kit. The spray formed a thin matrixed coating that adheres to the following surfaces: PVC tubings, polyethylene plastic bags, polyethylene and polyurethane made surgical gloves. All surfaces released iodine in vitro for about 10 hours when immersed in buffer solution pH 7.4 containing 0.05% KI.

EXAMPLE 2

Polyurethane Coating With Iodine Complexed Therein

The catheter is first coated with noniodine loaded polyurethane by the dipping thereof in a tetrahydrofuran solution containing 1.5 grams of segmented polyurethane (Estane, TM, Goodrich, Cleveland, Ohio).

Iodine is then complexed into the polyurethane coating by immersing the coated catheter in a 20% iodine/potassium iodide ($I_2$/KI) solution in water. The impregnated polyurethane-iodine complex coating is then dried in room air.

The resulting polyurethane-iodine complex coating may then be further coated with a noniodized Ethylene Vinyl Acetate (EVAc) by dipping the coated catheter in a chloroform solution of EVAc. The EVAc coating of 0.05 mm prevents iodine release from the polyurethane-iodine complex polymer coating by sublimation.

EXAMPLE 3

Catheters were cleaned and dipped into a 2.5% solution of polymer containing 20% iodine based on the polymer mass. Polyurethane (PU) (Estane), Ethyl Vinyl Acetate (EVAc), and ethylcellulose were used as the polymer coating in tetrahydrofuran (THF), dichloromethane, and ethanol solutions, respectively. A uniform coating that strongly adhered to the catheter surface was obtained with each of the three polymers. The coated catheters were further treated by immersing each of them in a 5% iodine/potassium iodide water solution for additional iodine loading by complexation. The EVAc coated catheter was further coated with a PU iodine free coating by dipping the catheter into a 1% PU in THF. The in vitro release of iodine in a potassium iodide solution was determined at 37° C. and the time for 50% iodine release is given. The total mass increase and iodine content was as follows:

| Coating | Coating mass | Iodine loading | Release time (t 1/2) |
| --- | --- | --- | --- |
| ethylcellulose | 6.3 mg | 0.3 mg | 20 h |
| EVAc | 4.5 mg | 0.7 mg | 40 h |
| PU | 5.2 mg | 0.6 mg | 45 h |
| PU + Complex | 5.8 mg | 0.75 mg | 24 h |
| EVAc + coating | 5.3 mg | 0.7 mg | 62 h |

The catheters were loaded with a significant amount of iodine and 50% of the loaded iodine was released within the first two days in vitro. The PU matrix+complexed iodine coating rapidly released the complexed iodine, thus the t ½ was decreased. The EVAc double coated catheter had a longer t ½ because of the second coating which reduces the drug release rate from the coated surface.

The uniodized polyurethane coating absorbed an additional 0.15 mg iodine (about 25%) while the other polymers absorbed negligible amounts of complexed iodine. This experiment demonstrates the utilization of programmable iodine releasing system for catheter surfaces.

EXAMPLE 4

The purpose of this experiment was to evaluate the amount of iodine loaded on the matrix coating as a function of the iodine concentration in the polymer-iodine solution. The amount of polymer-iodine coating was also determined as a function of the number of dippings. To solutions of polyurethane (Estane, Goodrich) or ethylene vinyl acetate (EVAc, 40% hydrolyzed) in tetrahydrofuran (2.5 weight %) iodine crystals were added to form solutions containing 10, 20, 30, and 40 weight % of iodine based on the polymer mass. An endotracheal tube made of PVC (Portex) was dipped once in the solutions to coat an area of 10 cm². After solvent evaporation at room air for 30 minutes, the coating mass and the iodine loading were determined. The coating mass was determined by weighing the device before and after coating and the iodine loading was determined by dissolving the coating in THF and determining the iodine content by UV at 310 nm. When several dippings were made, the coating was dried for 30 minutes before the next dipping. Typical results are summarized below:

| % iodine in solution | Coating mass (mg) EVAc | Coating mass (mg) PU | % Iodine in coating EVAc | % Iodine in coating PU |
| --- | --- | --- | --- | --- |
| one dip | | | | |
| 10 | 65 | 70 | 7 | 8 |
| 20 | 56 | 55 | 14 | 13 |
| 30 | 48 | 50 | 18 | 21 |
| 40 | 34 | 37 | 24 | 25 |
| two dips | | | | |
| 10 | 110 | 123 | 7 | 8 |
| 20 | 96 | 92 | 13 | 13 |
| 30 | 80 | 85 | 17 | 18 |
| 40 | 62 | 65 | 22 | 23 |

This data show that the iodine loading is similar for both polymers and EVAc is as good as PU for matrix-iodine coatings. The iodine loading increases with the increase in the iodine concentration in the polymer solution. However, the increase in the iodine loading in the dried coating is not proportional to the iodine content in the polymer solution, but decreases with the increase in iodine concentration. This is explained by iodine evaporation during the solvent evaporation which increases with the decrease in the polymer content in the coating solution. The increase in the coating mass in the second dipping is less than double the amount of the first dipping. This is due to a partial dissolution of the first coating during the second dipping. This decrease in coating mass during subsequent dippings can be minimized when the second coating is made by (1) spraying the polymer-iodine solution which evaporates fast leaving a coating without mass loss; (2) the subsequent coating is made with a polymer solution in a solvent that is a non-solvent for the polymer of the prior coating. For example if the first coating is with THF soluble PU which is insoluble in dichloromethane, the second dipping will be in EVAc-iodine solution in dichloromethane.

EXAMPLE 5

The thickness of the coating which affects the total iodine loading can be determined either by subsequent dippings, dipping the device in higher polymer-iodine concentrations, or by spraying a larger amount of polymer-iodine solution on the device surface. In an experiment a venous catheter inserting sheath made of polyurethane (tube of 10 cm long, 0.3 cm in diameter, total outer surface area approximately 9.4 cm²) was coated on the outside by dipping the device in various concentrations of polymer-iodine solutions. Solutions of EVAc in THF in concentrations of 2.5, 5, 7.5 and 10 weight % containing 20 weight % iodine based on the polymer mass were used for coating. The total coating mass and iodine loading are as follows:

| Polym. Conc. | coating mass (mg) | iodine content (mg) | Coating thickness |
| --- | --- | --- | --- |
| 2.5% | 57 | 8 | <0.10 mm |
| 5.0% | 120 | 19 | 0.10 mm |
| 7.5% | 190 | 29 | 0.14 mm |
| 10.0% | 320 | 52 | 0.22 mm (not uniform) |

As seen, increase in the polymer concentration increases the coating thickness and the amount of coating material, as well as the iodine content per coating area. Increase in the polymer concentration increases the viscosity of the polymer and thus more polymer is attached to the catheter surface. The duration of iodine release from these coated devices increases with the increase in the thickness of the coating.

EXAMPLE 6

The rate of release from a coated surface was further shown to be controllable by depositing the polymer/iodine coating on culture cluster plates.

Polyurethane-iodine complex: 24 well culture cluster plates (Costar, Cambridge Mass.) were coated with polyurethane by spreading 50 microliters of polyurethane (PU) solution in tetrahydrofuran (THF, 2.5 weight %) per well. After solvent evaporation, a uniform thin coating of 0.4 mg/cm$^2$ was obtained. To each well 3 ml iodine-potassium iodide solutions were added and allowed to react for 60 minutes at room temperature. The solutions were discarded and the wells were rinsed with deionized water for 10 minutes and left to dry at room air for 24 hours. The iodine concentrations in the solution were 1.0M, 0.1M, 0.05M, 0.01M, and 0.001M; the potassium iodide concentrations were 1.5 times the molarity of iodine in the solutions. For each concentration a total of four (4) wells were used. The total amount of iodine absorbed in the PU-iodine complex was 4, 1, and 0.5 weight % (50, 12 and 5 microgram per well), based on the polyurethane coating, from 1, 0.1, and 0.05M iodine solution, respectively. The 0.01M and 0.001M solutions did not provide detectable amounts of iodine.

Iodine release was studied by adding into the wells 3 ml phosphate buffer pH 7.4 at 37° C., or in 0.01M potassium iodide solution at 25° C. The solutions were replaced frequently with fresh solutions and the iodine concentrations in the solutions were determined by UV absorption at 280 nm.

Figure 11:
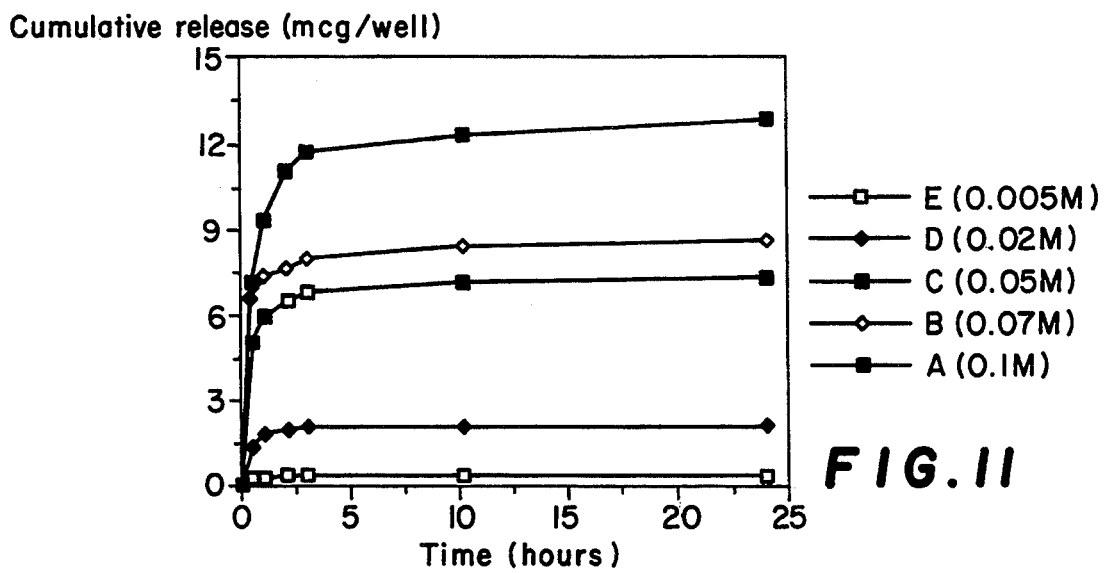
FIG. 11 is a graph of the rate of iodine release from a polymer iodine complex in phosphate buffer.
Figure 12:
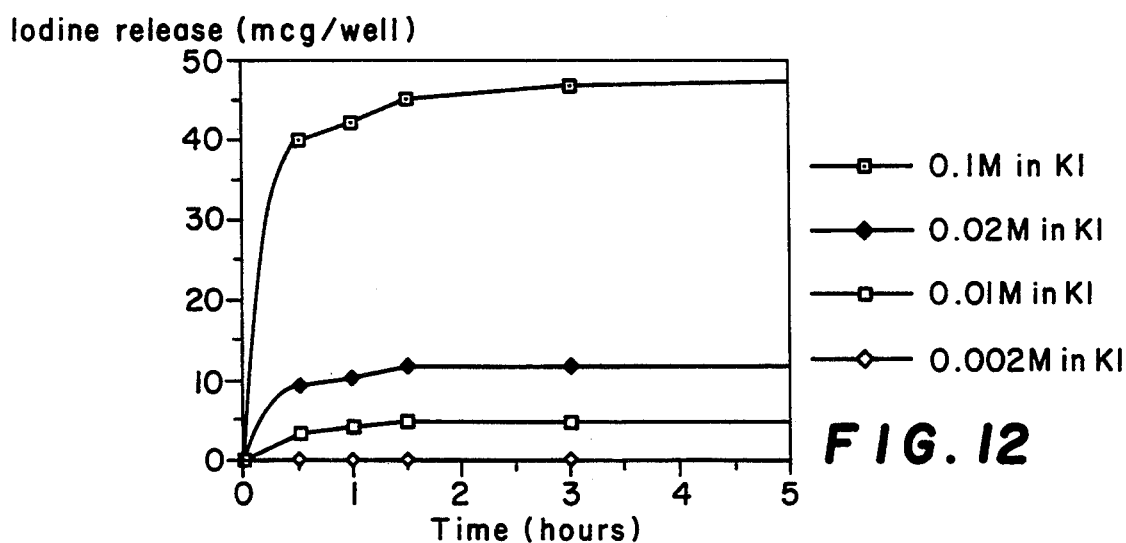
FIG. 12 is a graph of the rate of iodine release from a polymer iodine complex in potassium iodide.

The in-vitro release from polyurethane-iodine complex was rapid both in phosphate buffer and in potassium iodide solution. In phosphate buffer pH 7.4 at 37° C., iodine was released rapidly from the coating with about 90% of the iodine released in 3 hours, the remaining 10% was released constantly in the following 48 hours (FIG. 11). The release in potassium iodide solution was even faster and 90% of the iodine content was released in 1 hour. The increase in iodine release in potassium iodide solution was due to the higher solubility of iodine in potassium iodide solution (FIG. 12).

EXAMPLE 7

Having demonstrated that the catheters can be effectively coated with a polymer that is programmed to release iodine for periods that are long enough and at concentrations that are high enough to theoretically inactivate the HIV virus, the next experiment consists of effectively proving that the programmable-iodine releasing polymer is able to inactivate the virus. The programmable iodine-loaded polymer was tested using culture plates that are usually used in viral cultures.

Polyurethane-iodine matrix: 24 well plates (Costar) were coated with polyurethane-iodine by spreading 50 microliters of polyurethane-iodine (PU-iodine) solution in tetrahydrofuran (THF, 2.5 weight %) in each well. After solvent evaporation a dark coating was obtained. The iodine concentration in the polyurethane coating was 10, 20, and 30% based on the polyurethane. The total iodine content in the PU-iodine matrices was 120, 240 and 360 micrograms of iodine per well for the 10, 20 and 30 weight % PU-iodine coating. For each concentration, four wells were used.

Figure 13:
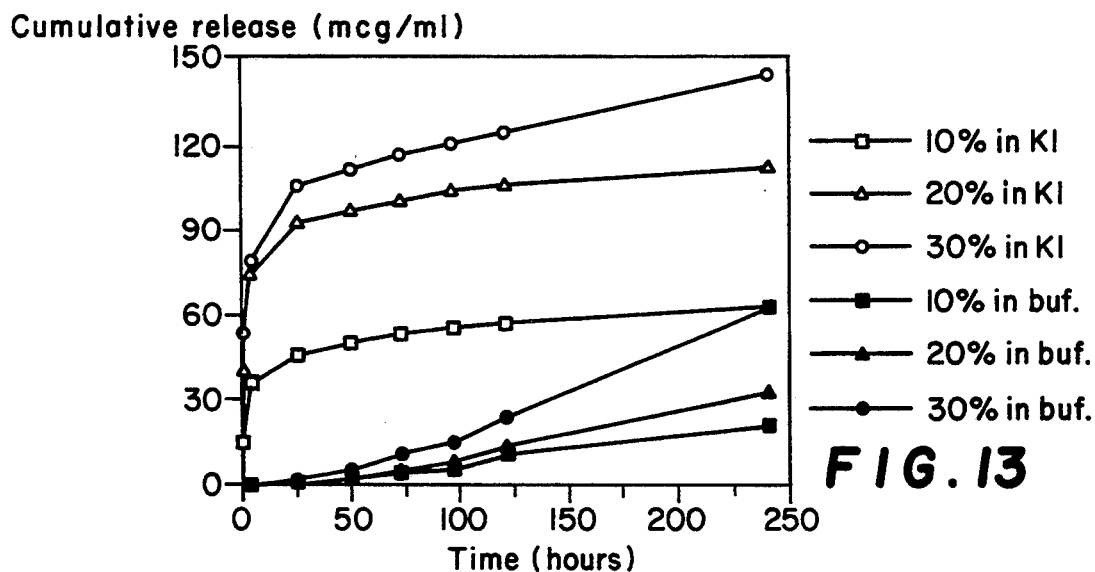
FIG. 13 is a graph of the rate of iodine release from a polymer iodine matrix in potassium iodide.

The release of iodine from the polyurethane-iodine matrix in phosphate buffer was very slow and was dependent on the solution in which the polymer is placed. In phosphate buffer solution, a negligible amount of iodine was released in 3 days. On the other hand, in potassium iodide solution, a significant amount of iodine was released for 10 days. About 70 to 80% of the iodine was released in 24 hours, and the rest was released constantly over a period of more than 10 days (FIG. 13).

By changing the thickness of the polymer coating and by using more than one polymer coating (e.g. using a combination of polyurethane-iodine matrix or polyurethane-iodine complexes, with a second coating of polyurethane-iodine complex or uniodized polymer), the amount and duration of iodine release can be programmed at the time of the coating. Using this approach, the duration of iodine release can be sustained for up to several months.

The effectiveness of the polyurethane-iodine coating has been demonstrated with HIV virus grown in tissue culture plates that have been coated with the complex coating of the present invention.

The in-vitro anti-HIV activity of the polyurethane-iodine coated plates was assessed by incubating HIV-3B virus in coated plates for 15 minutes, 30 minutes, 90 minutes, 3 hours, 6 hours, 12 hours and 24 hours prior to infection of the human lymphocyte (MT4) cells (5×100,000 cells/ml) at a multiplicity of infection of 100×tissue culture infections dose (TCID) 50. The plates were coated with polymers that release different concentrations of iodine; 1.8, 5.8, 7.3, and 9.2 µg of iodine/ml/hr. for at least the first few hours. The virus, and thus the coated plates, were diluted 1:20 before adding the cells. The infection was allowed to incubate at 37° C. for one hour, at which time the cells were diluted with culture medium RPM1 1640 supplemented with 10% heat-inactivated fetal bovine serum and 10% interleukin2 to a cell density of 8×10,000 cells/ml. The cells were then seeded onto 96-well plates and incubated at 37° C. Five days later, the cell-free supernatant was analyzed for reverse transcriptase and cells infected with virus exposed to plates coated with the present invention for 24 hours were analyzed for cell growth.

The MT4 cells that were exposed to the polyurethane-iodine complex multiplied as rapidly as control non-infected cells, indicating complete inactivation of the HIV.

Figure 14:
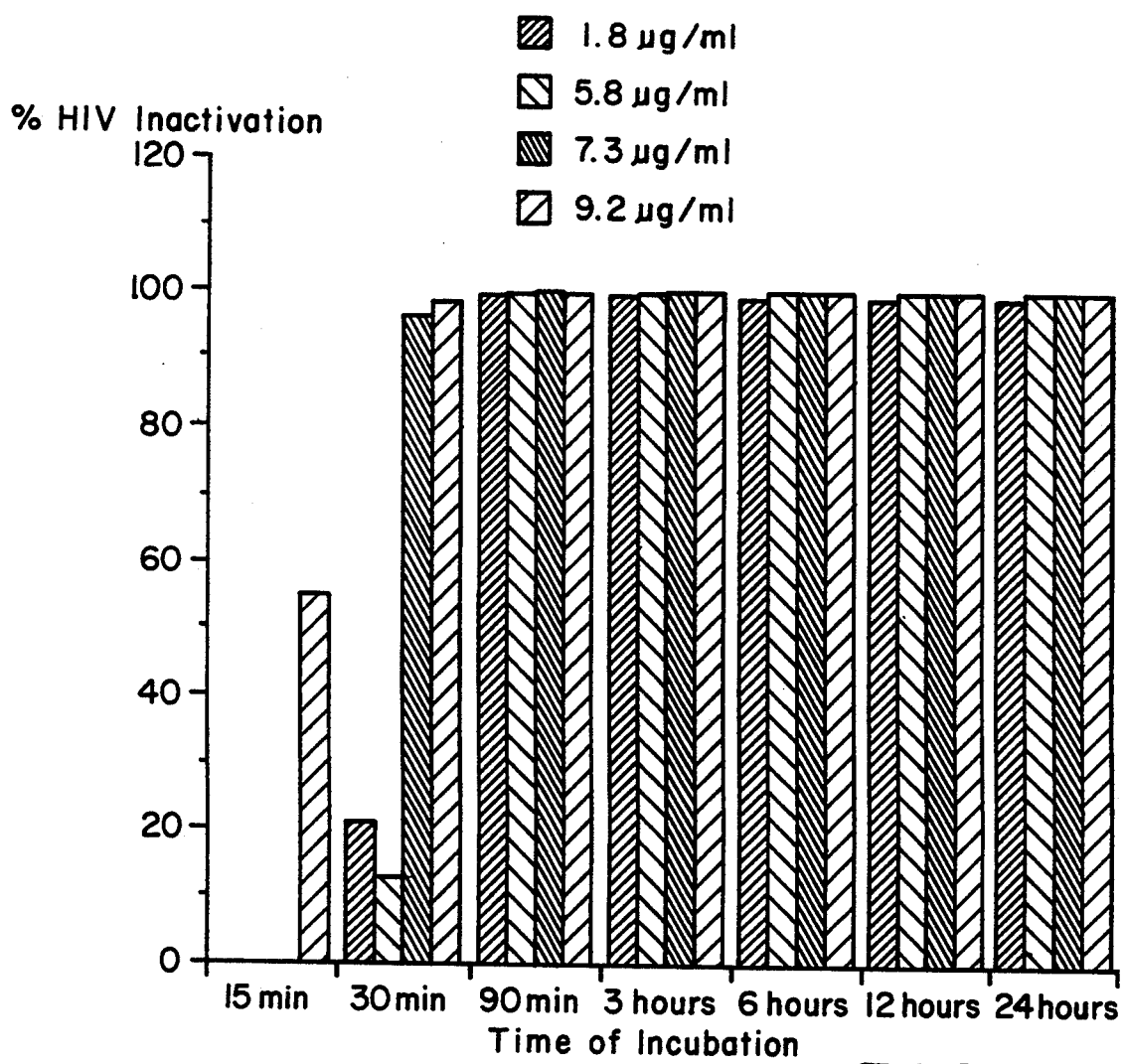
FIG. 14 is a bar chart of the inactivation of HIV virus by the coating of the present invention.

A quantitative analysis of the HIV inactivation was done in the polyurethane-iodine complex plates, by analyzing the cell-free supernatant for reverse transcriptase (RT). The data are tabulated in Table I below and summarized in FIG. 14.

Table I indicates that while only partial inactivation of HIV 3B was achieved after 15 minutes incubation in plate number 4, full inactivation of the virus was observed after only 30 minutes incubation in both plates 3 and 4. Complete inactivation of the virus was achieved in all plates after 90 minutes incubation and continued through 24 hours incubation. Interestingly, the cells exposed to virus incubated in the plates for 24 hours grew as rapidly as uninfected cells, indicating that the iodine released in the media did not affect the growth of the MT4 cells themselves.

TABLE I

| Analysis of HIV Inactivation by Reverse Transcriptase (RT) assay | |
|---|---|
| cpm (average of 3 wells) | % Inhibition of HIV |

15 minute incubation

TABLE I-continued
Analysis of HIV Inactivation by Reverse Transcriptase (RT) assay

| | cpm (average of 3 wells) | % Inhibition of HIV |
|---|---|---|
| Plate* | | |
| Control | 215350 | — |
| 1.8 μg Iodine/ml | 225358 | 0 |
| 5.8 μg Iodine/ml | 234782 | 0 |
| 7.3 μg Iodine/ml | — | — |
| 9.2 μg Iodine/ml | 96907 | 55 |
| 30 minute incubation Plate | | |
| Control | 229862 | — |
| 1.8 μg Iodine/ml | 183397 | 21 |
| 5.8 μg Iodine/ml | 201128 | 13 |
| 7.3 μg Iodine/ml | 13219 | 96 |
| 9.2 μg Iodine/ml | 4931 | 989 |
| 90 minute incubation Plate | | |
| Control | 285898 | — |
| 1.8 μg Iodine/ml | 1489 | 99.5 |
| 5.8 μg Iodine/ml | 950 | 99.7 |
| 7.3 μg Iodine/ml | 648 | 99.8 |
| 9.2 μg Iodine/ml | 923 | 99.7 |
| 3 hour incubation Plate | | |
| Control | 259064 | — |
| 1.8 μg Iodine/ml | 948 | 99.7 |
| 5.8 μg Iodine/ml | 739 | 99.7 |
| 7.3 μg Iodine/ml | 512 | 99.8 |
| 9.2 μg Iodine/ml | 622 | 99.8 |
| 6 hour incubation Plate | | |
| Control | 147961 | — |
| 1.8 μg Iodine/ml | 1731 | 99 |
| 5.8 μg Iodine/ml | 917 | 99.4 |
| 7.3 μg Iodine/ml | 621 | 99.6 |
| 9.2 μg Iodine/ml | 460 | 99.7 |
| 12 hour incubation Plate | | |
| Control | 147961 | — |
| 1.8 μg Iodine/ml | 1731 | 99 |
| 5.8 μg Iodine/ml | 917 | 99.4 |
| 7.3 μg Iodine/ml | 621 | 99.6 |
| 9.2 μg Iodine/ml | 460 | 99.7 |
| 24 hour incubation Plate | | |
| Control | 131116 | — |
| 1.8 μg Iodine/ml | 1970 | 98.5 |
| 5.8 μg Iodine/ml | 859 | 99.4 |
| 7.3 μg Iodine/ml | 636 | 99.5 |
| 9.2 μg Iodine/ml | 552 | 99.6 |
| Mock-Infected Plate | cpm | |
| Control | 559 | |
| 1.8 μg Iodine/ml | 565 | |
| 5.8 μg Iodine/ml | 503 | |
| 7.3 μg Iodine/ml | 531 | |
| 9.2 μg Iodine/ml | 501 | |

*concentrations are prior to dilution

The anti-HIV effectiveness of the coating of the present invention is further shown by the following: Commercially available central venous catheters (obtained from Baxter Pharmaceuticals), were coated with polyurethane-iodine complexes. Coated and control uncoated catheters were divided into 0.9 cm pieces, the surface of each piece being equivalent to the surface of each of the wells in the culture plates. The catheter pieces were exposed to UV radiation to sterilize the pieces. The pieces of catheter were then coated with a complexed polymer containing 9.2 μg iodine/ml. For inactivation of HIV, it is preferred that the catheter be coated on both the inside and outside surfaces. Since the catheter tube is coated both on the inside and on the outside, this would correspond to an area of about 1.77 cm². Several experiments were performed, each involving MT4 cells, using the HIV-1, strain 3B, as the virus inoculum.

Experiment 1: Catheter pieces were immersed in virus solution for 15, 30, 90, and 120 minutes and then the catheter pieces were used to inoculate MT4 cells. The cells were allowed to grow for 5 days at which time the cell-free supernatant was assayed for the presence of reverse transcriptase (RT). Table II presents the data obtained.

TABLE II
Measurement of Virus Remaining on Catheter Pieces after Incubation with HIV 3B

| Incubation Time minutes | Control Catheter RT cpm | Coated Catheter RT cpm |
|---|---|---|
| 15 | 6290 | 130 |
| 30 | 2576 | 108 |
| 90 | 1342 | 185 |
| 120 | 1080 | 242 |

The results indicated 97.93% inhibition of viral replication within 15 minutes in the coated group, as compared to the control, and this inhibition was sustained over 2 hours.

Experiment 2: MT4 cells were infected with HIV 3B for one hour, at which time the infected cells were exposed to catheter pieces. Five days later, the cell-free supernatant was assayed for the presence of RT as shown in Table III.

TABLE III
Ability of MT4 Cells to Support Viral Replication in the Presence of Catheter Pieces

| | Control Catheter | Coated Catheter |
|---|---|---|
| RT (cpm) | 24991 | 455 |

The results indicated 98.17% inhibition of viral replication in the coated group, as compared to the control.

Experiment 3: Catheter pieces were immersed in HIV 3B for 10 minutes. The catheter pieces were removed and kept at 100% humidity for 15 minutes, 30 minutes, 2 hours and 4 hours, at which time the catheter pieces were used to inoculate MT4 cells. Five days later, the cell-free supernatant was assayed for the presence of RT and the results are given in Table IV.

TABLE IV
Ability of Catheter Pieces to Retain Viable HIV 3B After Removal From Virus Solution

| Incubation Time minutes | Control Catheter RT cpm | Coated Catheter RT cpm |
|---|---|---|
| 15 | 184854 | 149 |
| 30 | 195101 | 108 |
| 120 | 176870 | 296 |
| 240 | 5997 | 103 |

The results indicated 99.91% inhibition of viral replication within 15 minutes in the coated group, as compared to control, and this inhibition was sustained over 4 hours.

Experiment 4: Catheter pieces were immersed in HIV 3B for 2 hours. At this time, the catheter pieces were removed and the virus was used in inoculate MT4 cells. Five days later, the cell-free supernatant was assayed for the presence of RT. The data is shown in Table V.

TABLE V

Ability of Catheter Pieces to Inactivate HIV 3B During 2 Hour Exposure Time

|  | Control Catheter | Coated Catheter |
|---|---|---|
| RT (cpm) | 45125 | 410 |

The results indicated 99.09% inhibition of viral replication in the coated group, as compared to the control.

Thus, it is evident that the amount of iodine released from the coated catheters is significant and is sufficient to inactivate the HIV virus.

EXAMPLE 8

Figure 15:
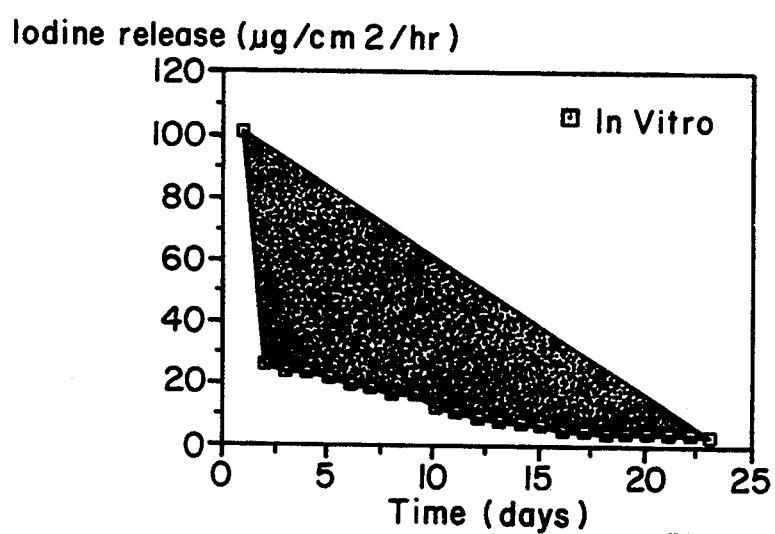
FIG. 15 is a graph of the in-vitro release of iodine from a polymer coating.

To demonstrate the effectiveness of the polymer-iodine coating on bacteria, the common and highly pathogenic human bacteria, Staphylococcus Aureus, was studied in-vitro and in-vivo (rats). The tip of a tracheal tube device was coated as follows: 0.5 grams of iodine crystals were dissolved in tetrahydrofuran solution containing 1.5 grams of segmented polyurethane PU (Estane). The tip of a tracheal tube, size 5.5 mm (Portex Inc., Wilmington, Mass.) was coated by dipping the tip in the iodine/polymer solution (total area 3 $cm^2$). After solvent evaporation, the dark uniform matrix coating of about 0.2 mm was coated with Ethylene Vinyl Acetate, (EVAc) coating by dipping in a chloroform solution of EVAc. The EVAc coating of 0.05 mm is to prevent iodine release from the surface by sublimation. Alternatively, the tube is first coated with polyurethane and then loaded with iodine by immersing the coated tube in a 20% $I_2$/KI solution in water. The impregnated PU/iodine complex coating was then dried in room air and coated with EVAc. In vitro iodine release was determined in 0.1M KI solution at 37° C. the iodine released in the solution was determined by UV absorption at 310 nm. The release of iodine from the tube is shown in FIG. 15.

The in vivo and biological activity of iodine released from the tube coating was then studied. Portions of an iodine-coated PVC tracheal tube were cut and subcutaneously implanted in 6 rats. The first 3 animals were sacrificed at day 7 and the devices were removed and placed for 3 consecutive days on an agar plate for antibacterial activity test as described below. At day 10, the tubes were placed in 20 ml 0.1M KI solution for in vitro release study. The antimicrobial activity was determined again at day 16. The second group of 3 rats were sacrificed at day 14 and the antimicrobial and the in vitro release was determined. The antimicrobial activity was determined using agar plates (Bactopepton 1%, yeast extract 0.5%) seeded with pathogenic Staphylococcus Aureus that was cultured from a patient's implanted catheter. The tubes were placed on the agar plate and incubated for 24 hours and the inhibition zone measured. The agar plates were replaced with fresh plates daily. The results are summarized in Table VI. As seen, the drug release is decreasing exponentially with time, but significant amounts of iodine are still released from the devices even after 23 days in vitro. All devices were active against bacteria for 21 days. The iodine release from the implantable devices after removal was lower when tested in vitro, which indicates that iodine is released faster in vivo. Histology of the site of implantation showed no irritation or tissue necrosis caused by the devices.

TABLE VI

In vitro, in vivo iodine release, and antibacterial activity of iodine-coated tubes:

| Time (days) | In vitro ($\mu g/cm^2/hr$) | In vivo (7 days) | In vivo (14 days) | Antibacterial activity (Inhibition zone, in mm) |
|---|---|---|---|---|
| 1 | 108 | I | I | 65* (no growth) |
| 2 | 25 | N | N | 65* (no growth) |
| 3 | 23 |   |   | 55* |
| 4 | 23 | V | V | 52* |
| 5 | 21 | I | I | 45* |
| 6 | 19 | V | V | 12# |
| 7 | 18 | O | O | 12# |
| 8 | 16 | 35* |   | 10# |
| 9 | 16 | 30* |   | 9# |
| 10 | 12 | 7# |   | 8# |
| 11 | 10 | 7# |   | 8# |
| 12 | 9 | 6# |   | 7# |
| 13 | 8 | 6# |   | 5# |
| 14 | 7 | 30* | 27* | 32* |
| 16 | 5 | 5.6# | 28* | 4.2# |
| 17 | 5 | 4.7# | 27* | 3.5# |
| 19 | 4 | 3.3# | 2.6# | 2.3# |
| 21 | 4 | 3.1# | 1.4# | 2.0# |
| 23 | 4 | 3# | inactive* | inactive* |

*Diameter of inhibition zone, mm
In vitro iodine release, ($\mu g/cm^2/hr$)

EXAMPLE 9

The stability of the polymer/iodine coating was demonstrated. Endotracheal tubes made of polyvinylchloride (Portex) were matrix coated with polyurethane-iodine and further coated with a rate-controlling second layer of plain polymer. Other endotracheal tubes were coated with a single polyurethane-iodine complex coat without a second layer. The coated tubes were each packed in a polyethylene sealed bag and stored at 4° C. and 25° C. The percent iodine remaining in each coated device was evaluated after one month of storage, by dissolving the iodine coating with tetrahydrouran (THF) and determining the iodine content by UV detection at 310 nm as compared to an iodine free endotracheal tube. The devices stored at 4° C. retained 98% and 92% of the original iodine respectively. The devices stored at 25° C. retained 95% and 75% of their iodine content after one month, respectively. After 12 months of storage at 25° C., the iodine content of the matrix coating retained more than 90% of the original iodine content, while the single polyurethane-iodine complex coat lost more than 50% of its original iodine content. This experiment demonstrates the advantage of using a second coating with respect to storage stability.

The polymer-iodine coating is effective when used with hepatitis B virus (HBV), other viruses, bacteria, fungi, mycobacteria and spores. Iodine is a universal anti-infective agent with no known microbial resistance. The coated catheter of the present invention protects the patient from infectious viruses and bacteria which may enter the patient while the catheter is inserted into either an incision in the skin of the patient or into a body cavity. The coated catheter of the present invention also protects health care providers from becoming infected from infectious viruses and bacteria which may be present on catheters which the health care provider contacts during or after removal of a catheter from the patient. A small abrasion, laceration or opening in the skin of the health care provider could be enough to allow the health care provider to be infected. The coated catheter of the present invention inhibits the viruses and bacteria to significantly reduce the probability of the health care provider becoming infected. Although catheters have been specifically identified, the coatings (complex, matrix and multiple) of the present invention may also be used on other instruments, equipment and supplies in the health services environment to inhibit infectious viruses, bacteria and germs.

What is claimed is:

1. An anti-infective coating for a catheter having a surface, the catheter being disposed and maintained within a body of a patient having blood or other body fluids, the anti-infective coating being insoluble in a biological medium and being bound to the surface of the catheter during storage, use and initial disposal thereof, the anti-infective coating comprising a biocompatible, non-hydrogel polymer, said polymer being compatible with and being bound to the surface of the catheter, said polymer being soluble in an organic solvent, and iodine complexed with the coating for programmed rapid release of the iodine from the coating when the catheter is disposed and maintained in the body of the patient and contacts the blood or other body fluids and further comprising a hydrophilic substance being added to the coating to increase the rate of release of the iodine from the coating, wherein the hydrophilic substance is a polyethylene glycol.

2. An anti-infective coating for a catheter having a surface, the catheter being disposed and maintained within a body of a patient having blood or other body fluids, the anti-infective coating being insoluble in a biological medium and being bound to the surface of the catheter during storage, use and initial disposal thereof, the anti-infective coating comprising a biocompatible, non-hydrogel polymer, said polymer being compatible with and being bound to the surface of the catheter, said polymer being soluble in an organic solvent, and iodine complexed with the coating for programmed rapid release of the iodine from the coating when the catheter is disposed and maintained in the body of the patient and contacts the blood or other body fluids, wherein the catheter is an implantable catheter.

3. The anti-infective coating of claim 2, wherein replication of human immunodeficiency virus is at least 98% inhibited in approximately 15 minutes by the coating.

4. The anti-infective coating of claim 2, wherein the polymer is selected from the group consisting of polyurethane and polyurea.

5. The anti-infective coating of claim 2, wherein the solvent is selected from the group consisting of alcohols, ketones, ethers, halogenated aliphatic hydrocarbons and aromatic hydrocarbons.

6. The anti-infective coating of claim 2, wherein the iodine loading is approximately 0.01% to 40% iodine.

7. The anti-infective coating of claim 2, wherein the coating has a thickness, the thickness being approximately 0.1 to 0.22 mm.

* * * * *